United States Patent [19]

Carter

[11] Patent Number: 4,683,878
[45] Date of Patent: Aug. 4, 1987

[54] OSTEOSYNTHETIC FIXATION PLATE

[75] Inventor: Dennis R. Carter, Palo Alto, Calif.

[73] Assignee: Kirschner Medical Corporation, Timmonium, Md.

[21] Appl. No.: 728,185

[22] Filed: Apr. 29, 1985

[51] Int. Cl.[4] ............................................. A61F 5/04
[52] U.S. Cl. ........................... 128/92 YP; 128/92 YF
[58] Field of Search .............. 128/92 D, 92 R, 92 YP, 128/92 YM, 92 YF

[56] References Cited

U.S. PATENT DOCUMENTS

| 4,408,601 | 10/1983 | Wenk | 128/92 D |
| 4,429,690 | 2/1984 | Angelino-Pievani | 128/92 D |

FOREIGN PATENT DOCUMENTS

| 2131422 | 12/1971 | Fed. Rep. of Germany | 128/92 D |
| 2213283 | 8/1973 | Fed. Rep. of Germany | 128/92 D |
| 1051847 | 9/1953 | France | 128/92 D |
| 1239266 | 7/1960 | France | 128/92 D |
| 2233973 | 1/1975 | France | 128/92 D |
| 2367479 | 5/1978 | France | 128/92 D |
| 852322 | 8/1981 | U.S.S.R. | 128/92 D |
| 1107841 | 4/1982 | U.S.S.R. | 128/92 D |

OTHER PUBLICATIONS

Zimmer Inc., Warsaw, IN., 1947 Catalog, p. 29, (Sherman Type SMO Plates and Screws).

Primary Examiner—C. Fred Rosenbaum
Assistant Examiner—C. W. Shedd
Attorney, Agent, or Firm—Frost & Jacobs

[57] ABSTRACT

The present invention comprises an elongated bone fixation plate with a center portion which bridges the fracture site. The central portion has a square cross-sectional shape. Two oppositely directed end portions extend axially from the central portion. The central portion has a width which is substantially less than the width of the end portions of the bone fixation plate. The end portions of the bone fixation plate have a plurality of elongated holes and each end portion tapers in thickness from adjacent the central portion to the outer terminating ends of the fixation plate. The plurality of holes are elongated in nature with each hole having a vertical distal wall and an inclined proximal end wall sloping toward the vertical distal wall. Each end portion has a uniform width and the entire bottom surface of each end portion may be concave in shape so as to provide a complementary mating surface with the fractured bone. By employing cortical or cancellous bone screws having a head whose bottom surface is rounded, the bone fixation plate draws each bone piece toward one another and places the bone pieces in compression at the fracture site when the plate and screws are fully secured to the bone.

20 Claims, 8 Drawing Figures

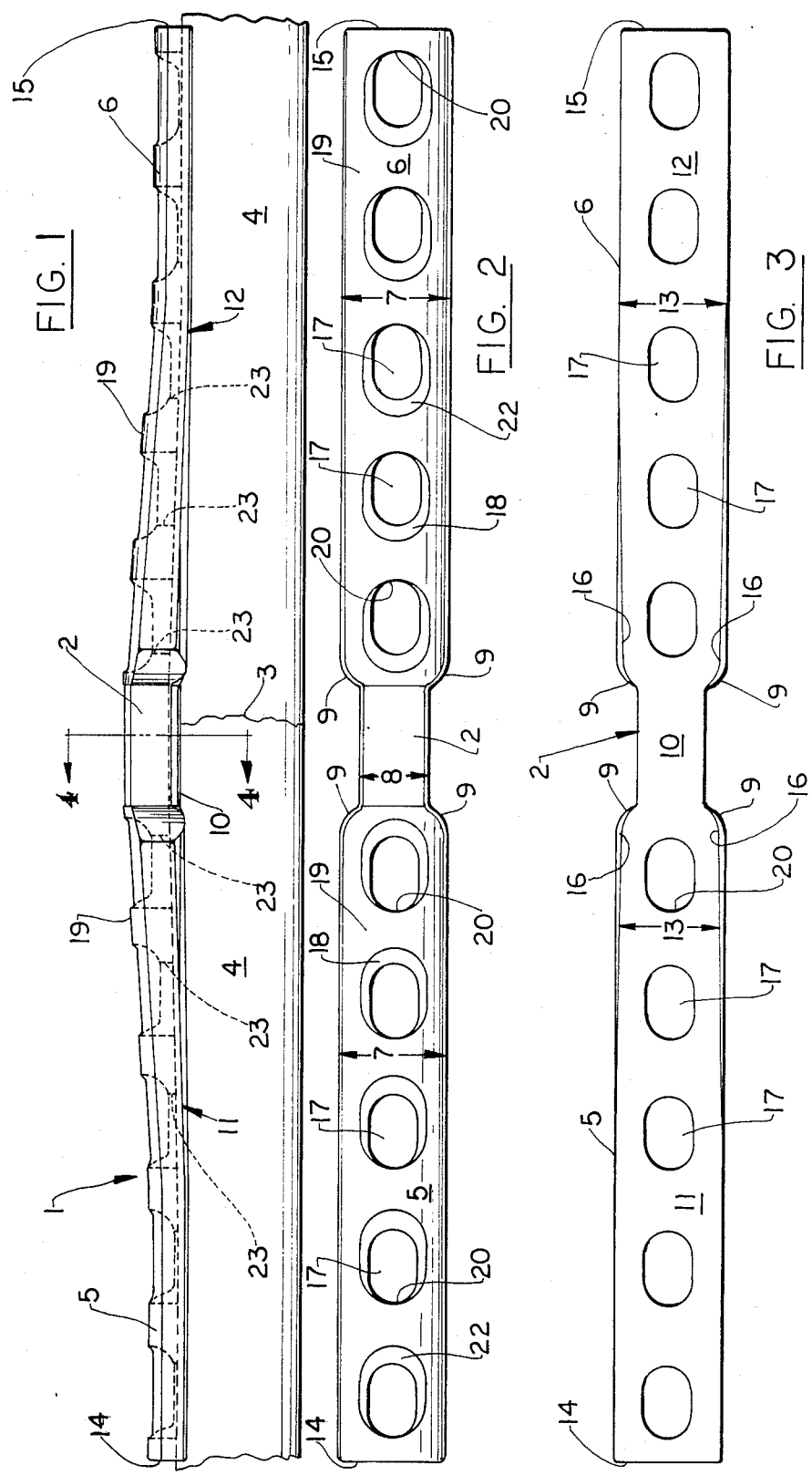

OSTEOSYNTHETIC FIXATION PLATE

BACKGROUND OF THE INVENTION (1) Field of the Invention

The present invention pertains to a plate for joining broken bones, and in particular, a plate designed to rigidly fix two bone parts in the correct anatomical position so as to permit the broken or disjointed bones to correctly heal.

(2) Prior Art

The use of internal osteosynthetic fixation plates and screws for long-bone fractures has been known as early as 1886. Many improvements have occurred over the years as a result of the direct observation of the progress of bone healing during the employment of fixation plates.

In the early stages of fracture healing with a fixation plate, the fracture site is exposed to eccentric axial forces which may result in high bending stresses in the fixation device that remain present until solid fracture healing is achieved. Especially high bending stresses may be encountered in the bone with severely comminuted fractures or in delayed unions having poor bone contact. High bending forces in the fracture fixation plate may result in motion at the fracture site and possible fatigue failure of the fixation plate before bone union is achieved. Because of this possible complication it is preferabe to utilize a device which has high bending stiffness and strength. To obtain better torsional stability at the fracture site, it is also preferable to use a device which has a large torsional rigidity and torsional strength. Also, in the early stages of fracture healing, the vascular demands of the injured bone are great, and, in order to promote more rapid fracture healing, the vascular supply to the fracture site should be disturbed as little as possible. In the case of bone plating, this can be achieved by using a more narrow plate particularly at the fracture point.

In the late stages of fracture healing, the bone is capable of sharing the axial forces with the fixation plate. However, if the actual stiffness of the plate is high, the plate will "overprotect" the bone and the bone will become osteoporotic, making it more susceptible to refracture after plate removal. This complication may be avoided by the use of a fixation plate with low axial stiffness. Thus, a perfect fixation plate has high bending stiffness and strength, large torsional rigidity and torsional strength, and low axial stiffness.

Fracture fixation plates which are now known and in use fail to meet the requirements of bone fracture mending in a number of ways. The axial stiffness or rigidity of an implant device is proportional to its cross-sectional area and therefore directly proportional to plate thickness and width. The bending rigidity and strength are proportional to a power function of the thickness. Since conventional plates are much wider than they are thick, they have a high axial stiffness and strength and relatively poor bending stiffness and strength. In addition, the width of the plate may significantly disturb the vascular supply to the fracture site. The following patents are illustrative of prior art devices.

French Pat. No. 1,051,847 issued to Carrieri discloses a bone fixation plate comprising three members, namely, two identical base members and an internally threaded union element. Each base member includes a portion which contacts the bone. At one end of each base member there is an upwardly extending, non-contacting threaded projection. Each base member is attached to the bone on opposite sides of the fracture site in axial alignment with one another. The internally threaded union member is then threaded onto each of the threaded projections which face one another to draw each base member together, and thus the corresponding bone pieces toward one another, to assure good contact between the bone pieces at the fracture site. This device has poor bending rigidity because of its wide width and small thickness, and additionally, there is some sloppy movement because the stress is concentrated at the threads.

U.S. Pat. No. 3,528,085 to Reynolds, Jr. discloses a one-piece bone compression plate having a plurality of screw holes. The pair of holes which straddle the fracture site are elongated and include a sliding ramp. When the bone compression plate is properly positioned with screws inserted in each elongated hole straddling the fracture site, the bone is placed in compression at the fracture site by tightening the screws forcing them to slide down their respective ramps thereby drawing the bone pieces toward one another and placing them in compression. The bone compression plate has a large uniform width and a small constant thickness. Thus it disturbs the vascular supply to the fracture site and has poor bending rigidity and strength at the fracture site since the plate is greater in width than in thickness.

U.S. Pat. No. Re. 28,841 to Allgower, et al discloses an osteosynthetic pressure plate having a plurality of elongated screw holes at each end of the pressure plate. Each screw hole has an oblique portion designed to be engaged by the underside of a semispherical head of a bone-fixing screw. The plate secured with screws will hold the bone parts in compression by drawing each bone part toward one another in tight engagement. The bone-fixing screws must have a head whose underside is semispherical in form so as to slide down the oblique portion of each elongated screw hole of the pressure plate. Additionally, the bone fixation pressure plate has a large uniform width and a small uniform thickness so that no increase in bending strength is obtained. Also, the vascular supply at the fracture site is reduced since the compression plate has a large uniform width.

French Pat. No. 2,367,479 to De Bazelaire discloses a bone fixation plate which is thicker at the center and gradually tapers toward each end thereof. This plate has a uniform width, and the underside thereof may be curved to more fully correspond with the shape of the bone. While this plate does have good bending rigidity and strength, the plate has high axial stiffness and prevents good vascular supply to the fracture site since the width of the plate is constant.

SUMMARY OF THE INVENTION

The bone fixation plate of the present invention has a plurality of elongated screw holes to securely fasten the plate to a fractured bone or to a bone in need of modeling or support. The elongated bone fixation plate has a generally square cross-sectional shape at its central portion which spans or bridges the fracture site. This provides increased torsional stiffness and strength and increased bending strength over the prior art devices. Additionally, the center portion is narrower in width than the remainder of the fixation plate, so as to provide good vascular supply to the fractured site. The elongated fixation plate tapers from the maximum thickness adjacent the center portion of the plate, to each distal end portion thereby increasing the bending strength from the distal ends toward the center of the fixation plate. The plurality of elongated holes are shaped such that the distal end of each hole is a substantially vertical wall while the proximal end of each elongated hole has an inclined concave surface designed to mate with the semispherical bottomside of the head of a screw. Optionally, the proximal end of each elongated hole could include an inclined convex surface so as to bulge outwardly toward the interior of the hole.

In the broadest sense, the present invention comprises an elongated fixation plate with a central portion which bridges the fracture site. The central portion has a square cross-sectional shape, whose width is substantially less than that of the remaining width of the fixation plate. The end portions of the plate, which are integral and in alignment with the two ends of the central portion, have a plurality of elongated holes. Each end portion tapers in thickness from adjacent the central portion to the outer distal ends of the fixation plate and is uniform in width. The plurality of holes are elongated in nature with each hole having a vertical distal wall with respect to the central portion of the fixation plate, while the proximal wall of each hole includes an oblique surface or ramp sloping toward the vertical distal wall. Optionally, the entire length of the bottom surface of the fixation plate is concave in shape so as to provide a contact surface which complementary mates with the bone.

The present invention will be more fully understood and described with reference to the following drawings and complete description.

BRIEF DESCRIPTION OF THE DRAWINGS

FIG. 1 is a side view of a fractured bone with the bone fixation plate of the present invention attached thereto.

FIG. 2 is a plan view of the bone fixation plate of the present invention.

FIG. 3 is a bottom view of the bone fixation plate of the present invention.

DESCRIPTION OF THE PREFERRED EMBODIMENTS

Figure 4:
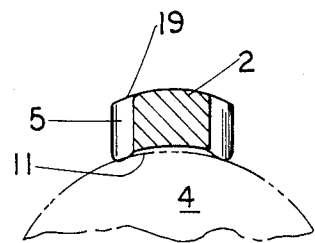
FIG. 4 is a cross-sectional view taken along line 4—4 of FIG. 1.

The osteosynthetic fixation plate of the present invention is generally illustrated by reference numeral 1, in FIG. 1. The osteosynthetic plate 1 is an elongated bone fixation plate having a central portion 2 which is generally substantially square in cross-sectional shape as best illustrated in FIG. 4. The central portion 2 is that portion of the bone fixation plate 1 designed to bridge or span the fracture site 3 of the bone 4.

A pair of axial end portions 5 and 6 extend longitudinally from each end of the central portion 2. As illustrated in FIG. 2, the axial end portions 5 and 6 have a uniform width 7 which is larger than the width 8 of the central portion 2. The bone fixation plate 1 includes a pair of matching tapered portions 9 which extend from each end of the central portion 2 to each axial end portions 5 and 6. As best illustrated in FIG. 1, the bone fixation plate 1 also tapers in thickness from each distal end of each axial end portions 5 and 6 to the center portion 2. The increased thickness of end portions 5 and 6 levels off adjacent the central portion 2. Thus, the bone fixation plate tapers in thickness from each distal end of end portions 5 and 6, to approximately the central portion 2, at which point it is uniform in thickness. Therefore, central portion 2 is generally thicker and narrower in width than the remaining axial end portions 5 and 6 of the bone fixation plate 1. As stated previously, the central portion 2 has a square cross-sectional area, while each remaining axial end portion 5 and 6 has a rectangular cross-sectional area whose width is substantially larger than the height or thickness.

The central portion 2 has a bottom surface 10, as illustrated in FIGS. 1 and 3. The bottom surface 10 may be planar with the bottom surfaces 11 and 12 of end portions 5 and 6, respectively. Preferably, however, the bottom surface 10 is incapable of contacting the bone 4 in the fully secured position. This is because the bottom surface 10 of the central portion 2 is not planar with respect to the bottom surfaces 11 and 12 of the end portions 5 and 6. This allows excellent vascular supply to the fracture site because the central portion 2 in effect bridges or spans the fracture site without contacting it.

While the width of the end portions 5 and 6 is constant, the bone contacting width 13 of the bottom surfaces 11 and 12 may not be constant, as best illustrated in FIG. 3, for the reasons set forth hereinafter. At the terminal ends 14 and 15 of the end portions 5 and 6, respectively, the bone contacting width 13 is larger than adjacent the central portion 2. This is because the edges 16 of the bone contacting width 13 adjacent the central portion 2 have been rounded so that the actual contacting width 13 convergingly tapers from the terminal ends 14 and 15 to the central portion 2. Thus, the rounded edges 16 actually reduce the bone contacting width 13. If rounded edges are employed, the effect is to further aid in permitting an increase in blood supply to the fracture site, because the actual contact width 13 convergingly tapers resulting in less surface area of the bone plate 1 contacting the bone. Thus, vascular vessels can grow at the fracture site as well as adjacent it, to increase the blood supply.

Each axial end portion 5 and 6 is provided with a plurality of holes 17 which are elongated in the longitudinal direction of the bone fixation plate 1. The number of holes employed depends upon the elongated length of the bone fixation plate 1. Each hole 17 is countersunk by a beveled surface 18 so that a bone-screw will not project above the upper surface 19 of the bone fixation plate 1 when fully secured to the bone 4.

Figure 6:
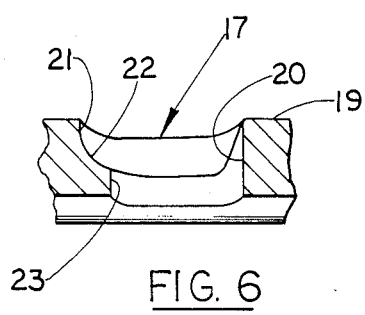
FIG. 6 is an enlarged, fragmentary, longitudinal cross-sectional view of a screw hole as illustrated in FIG. 1.
Figure 7:
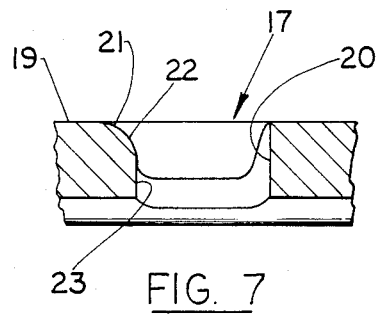
FIG. 7 is an enlarged, fragmentary, longitudinal cross-sectional view of a modification of the screw hole of the bone fixation plate.

The elongated holes 17, as illustrated in FIG. 2, include a distal end 20 and a proximal end 21. As illustrated in FIGS. 2, 6 and 7, the distal end 20 is substantially vertical when the bone fixation plate is substantially horizontal. As best illustrated in FIG. 6, the proximal end 21 of each hole 17 is inclined, as illustrated by reference numeral 22, from the upper surface 19 of the bone fixation plate 1 to the bottom surfaces 11 and 12 thereof. As best illustrated in FIG. 2, the inclined surface or ramp 22 gradually extends from the proximal end 21 to the distal end 10, at which point it is non-existent, thus creating a vertical wall. The inclined surface 22 of each hole 17 is uniform with respect to all other holes. As shown in FIG. 1, the bottom incremental thickness 23 of each hole 8 varies in height from the terminal ends 14 and 15 of the end portion 5 and 6, where it is practically non-existent, to the holes 17 adjacent the central portion 2 where the incremental thickness 23 is substantial. This is due to the fact that the thickness of the fixation plate increases from each terminal end 14 and 15 to the central portion 2.

The screws 24 designed to securely fasten the bone fixation plate 1 to the bone 4 are the type which have a semispherical head 25, i.e., the bottom portion 26 of each screw head is semispherical in shape. When the bottom portion 26 of the screw 24 engages the inclined surface or ramp 22, during insertion of the screw into the bone, relative movement between the screw 24 and the plate 1 occurs to place both bone pieces 4 in compression with one another.

The square cross-sectional shape of the central portion 2 of the bone fixation device provides good bending and torsional strength of the bone fixation device, thus optimizing fatigue resistance and its bending and torsional rigidity with respect to conventional fixation plates. The increase in bending and torsional rigidity results in more stability and less movement at the fracture site. The width of the central portion 2 of the bone fixation device 1 is less than that of conventional bone fixation plates and therefore the vascular blood supply to the fracture site 3 will be greater with the device of the present invention, resulting in more rapid healing, particularly since the rate of healing is strongly dependent upon blood supply. The significantly improved behavior of the bone 4 in bending and torsion is achieved without increase in axial stiffness of the device 1 when compared to conventional bone fixation plates having a constant width because the overall cross-sectional area of the central portion 2 is identical with that of conventional prior art devices. In other words, the cross-sectional area of the present invention is substantially the same as those employed in conventional devices because the thickness has increased. This results in good bending and torsional strengths, while achieving an increase in blood supply to the fracture site 3 because the width of the central portion 2 of the bone fixation device 1 is generally narrower adjacent the fraction site than that of prior art devices and the central portion 2 does not contact the bone 4 at the fracture site 3.

Figure 5:
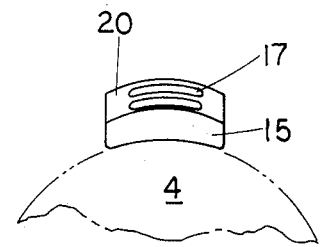
FIG. 5 is an end view of the bone fixation plate of the present invention.

As illustrated in FIGS. 4 and 5, the bottom surfaces 11 and 12 of the bone fixation plate 1 may be curved so as to more fully complement the curved surface of the bone 4. The radius of curvature may be varied depending upon the size of bone to which the bone fixation plate is to be applied.

Figure 8:
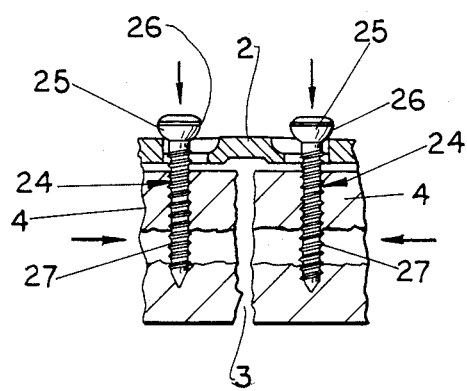
FIG. 8 is a fragmentary cross sectional view of the bone fixation plate being attached to a bone at the fracture site.

The holes 17 are designed to securely fasten the bone fixation plate 1 to the bone 4, when a semispherical head 25 of a screw 24 is employed. The bone screw 24 is inserted into the hole 17 at the distal end 30 so that its threads 27 contact the vertical wall of the distal end 20. When the bottom portion 26 of the semispherical head 25 of the screw 24 comes into contact with the inclined surface 22 of the bone fixation plate 1 adjacent the distal end 20, as best illustrated in FIG. 8, it will be necessary to insert another screw 24 into another hole 17, opposite the fracture site 3 from the first screw. Further advancement of both bone screws into the bone 4 causes the screws to axially or longitudinally move in the direction of the fracture 3 drawing the bone pieces together and place them in compression with one another. Additional holes 17 in each end portion 5 and 6 may provide displacement of the bone pieces toward one another in incremental steps. In this manner, when more than two holes exist, each additional screw which is secured to the bone will cause displacement of its associated bone piece toward the other by a fixed amount, which in total will provide the necessary compression force at the fracture site.

While the inclined surface 22 illustrated in FIG. 6 is concave, it may also be convex (as illustrated in FIG. 7) or a planar ramp. Thus, the most important feature of the inclined surface 22 is not whether it is concave, convex or planar, but that it gradually slopes or inclines from the distal end 20 of each hole 17 to the proximal end 21, so that the natural effect of securing the bone fixation plate 1 to the bone 4 results in the bone pieces being placed in compression at the fracture site.

The typical conventional plate has a width four times its thickness throughout its length, while the fixation plate of the present invention has a square cross-section with reduced width throughout the central portion of the plate resulting in an increase in axial rigidity as compared to conventional plates.

In order to achieve low axial stiffness so that the bone fixation plate does not overprotect the bone, causing the bone to become osteoporotic under the plate, it is important to employ a material which has a high bending and torsional strength, yet is characterized in that it has low axial stiffness. In conventional bone fixation plates, the plates were formed of stainless steel because of its resistance to chemical attack and its superior strength. With the present invention, it was discovered that stainless steel has a great axial stiffness. Preferably, the bone fixation plate of the present invention is made from a metal having a low axial stiffness, namely, TI-6AL-4V alloy, i.e., an alloy having a titanium base with 6% by weight aluminum and 4% by weight vanadium. It has been found that this metal has low axial stiffness and relatively high bending rigidity and strength, with a large torsional rigidity and strength. Hence it is the preferred material for constructing the osteosynthetic bone fixation plate of the present invention.

Modification of the present invention may be made without departing from the spirit of it.

What is claimed is:

1. An osteosynthetic bone fixation plate for securing fractured or disjointed bones, comprising:

a unitary, elongated, rigid plate having a central portion of sufficient length to bridge a fracture site, said central portion having a substantially square cross-sectional shape throughout its length, and two oppositely directed end portions, each of which extends axially from said central portion to a terminating end, said end portions having a width greater than said central portion and having a thickness which decreasingly tapers from said central portion to said terminating ends, said end portions also having a plurality of elongated holes, each of said holes having a vertical distal end wall and an inclined proximal end wall, whereby said plate, when secured to said fractured bones with a plurality of bone screws, places said fractured bones in compression with respect to one another at said fracture site.

2. The bone fixation plate of claim 1, further including a tapered portion extending between said central portion and each of said oppositely directed end portions so that said plate gradually increases in width from said square cross-sectional central portion to said oppositely directed end portions.

3. The bone fixation plate of claim 1, wherein said holes include a beveled edge so that said screws are countersunk when fully secured to said fractured bones.

4. The bone fixation plate of claim 1, wherein said inclined proximal end wall of said hole is concave.

5. The bone fixation plate of claim 1, wherein said inclined proximal end wall of said hole is convex.

6. The bone fixation plate of claim 1, made from an alloy having a titanium base with a 6%, by weight, aluminum, and 4%, by weight, vanadium.

7. The bone fixation plate of claim 1, wherein each of said holes is identically sized and in axial alignment with one another.

8. The bone fixation plate of claim 1, wherein said unitary, elongated, rigid plate has a bottom surface which is curved concavely so as to complementary mate with the surface of said fractured bones.

9. The bone fixation plate of claim 1, wherein said central portion and said two oppositely directed end portions have bottom surfaces, said bottom surface of said central portion is non-planar with said bottom surfaces of said two oppositely directed end portions, to prevent said plate from contacting said bones at said fracture site.

10. The bone fixation plate of claim 9, wherein said bottom surfaces of said two oppositely directed end portions have rounded edges adjacent said central portion to aid in increasing the vascular supply adjacent said fracture site.

11. An osteosynthetic bone fixation device for securing fractured bones, comprising a unitary, elongated, rigid plate and a plurality of cortical or cancellous bone screws, said unitary, elongated plate having a central portion of sufficient length to bridge a fracture site, said central portion having a substantially square cross-sectional shape throughout its length, and two oppositely directed end portions, each of which extends axially from said central portion to a terminating end, said end portions having a width greater than that of said central portion and having a thickness which decreasingly tapers from said central portion to said terminating ends, said end portions also having a plurality of elongated holes, each of said holes having a vertical distal end wall and an inclined proximal end wall, said bone screws having an elongated threaded portion and a head at one end thereof, said head having a bottom surface which is rounded so as to slidingly mate with said inclined proximal end wall, whereby said plate, when secured to said fractured bones with a plurality of said bone screws, places said fractured bones in compression with respect to one another at said fracture site.

12. The bone fixation plate of claim 11, further including a tapered portion extending between said central portion and each of said oppositely directed end portions so that said plate gradually increases in width from said square cross-sectional central portion to said oppositely directed end portions.

13. The bone fixation plate of claim 11, wherein said holes include a beveled edge so that said screws are countersunk when fully secured to said fractured bones.

14. The bone fixation plate of claim 11, wherein said inclined proximal end wall of said hole is concave.

15. The bone fixation plate of claim 11, wherein said inclined proximal end wall of said hole is convex.

16. The bone fixation plate of claim 11, made from an alloy having a titanium base with a 6%, by weight, aluminum, and 4%, by weight, vanadium.

17. The bone fixation plate of claim 11, wherein each of said holes is identically sized and in axial alignment with one another.

18. The bone fixation plate of claim 11, wherein said unitary, elongated, rigid plate has a bottom surface which is curved concavely so as to complementarily mate with the surface of said fractured bones.

19. The bone fixation plate of claim 11, wherein said central portion and said two oppositely directed end portions have bottom surfaces, said bottom surface of said central portion is non-planar with said bottom surfaces of said two oppositely end portions, to prevent said plate from contacting said bones at said fracture site.

20. The bone fixation plate of claim 19, wherein said bottom surfaces of said two oppositely directed end portions have rounded edges adjacent said central portion to aid in increasing the vascular supply adjacent said fracture site.

* * * * *